(12) United States Patent
Biemans et al.

(10) Patent No.: US 8,933,218 B2
(45) Date of Patent: Jan. 13, 2015

(54) CONJUGATION PROCESS FOR PNAG AND A CARRIER PROTEIN

(75) Inventors: Ralph Leon Biemans, Rixensart (BE); Pierre Duvivier, Rixensart (BE); Tomas Maira-Litran, Boston, MA (US)

(73) Assignee: GlaxoSmithKline Biologicals s.a. (BE)

( * ) Notice: Subject to any disclaimer, the term of this patent is extended or adjusted under 35 U.S.C. 154(b) by 1217 days.

(21) Appl. No.: 12/294,643

(22) PCT Filed: Mar. 29, 2007

(86) PCT No.: PCT/EP2007/053060
§ 371 (c)(1),
(2), (4) Date: Sep. 26, 2008

(87) PCT Pub. No.: WO2007/113224
PCT Pub. Date: Oct. 11, 2007

(65) Prior Publication Data
US 2010/0303852 A1    Dec. 2, 2010

Related U.S. Application Data

(60) Provisional application No. 60/787,587, filed on Mar. 30, 2006, provisional application No. 60/787,249, filed on Mar. 30, 2006.

(30) Foreign Application Priority Data

Mar. 30, 2006  (GB) .................................. 0606416.6
Mar. 30, 2006  (GB) .................................. 0606417.4

(51) Int. Cl.
| | | |
|---|---|---|
| A61K 39/385 | (2006.01) | |
| A61K 39/085 | (2006.01) | |
| A61K 39/02 | (2006.01) | |
| C07H 1/00 | (2006.01) | |
| A61K 39/38 | (2006.01) | |
| A61K 39/00 | (2006.01) | |
| A61K 31/70 | (2006.01) | |
| A61K 47/48 | (2006.01) | |

(52) U.S. Cl.
CPC ....... *A61K 39/085* (2013.01); *A61K 2039/6037* (2013.01); *A61K 2039/55577* (2013.01); *A61K 2039/55555* (2013.01); *A61K 47/48261* (2013.01); *A61K 2039/55544* (2013.01); *A61K 2039/55572* (2013.01); *A61K 47/48284* (2013.01); *A61K 47/4833* (2013.01); *Y10S 424/831* (2013.01)
USPC ................ 536/123.1; 424/197.11; 424/194.1; 424/831; 424/243.1; 424/237.1; 514/23

(58) Field of Classification Search
None
See application file for complete search history.

(56) References Cited

U.S. PATENT DOCUMENTS

| | | | |
|---|---|---|---|
| 8,703,148 B2 * | 4/2014 | Biemans et al. ........... | 424/194.1 |
| 2005/0118198 A1 | 6/2005 | Pier et al. | |
| 2009/0162341 A1 * | 6/2009 | Foster et al. ................ | 424/94.63 |

FOREIGN PATENT DOCUMENTS

| | | |
|---|---|---|
| WO | WO 03/053462 | 7/2003 |
| WO | WO 2005/016973 | 2/2004 |
| WO | WO 2004/043405 | 5/2004 |
| WO | WO 2004/080490 | 9/2004 |

OTHER PUBLICATIONS

Fattom, et al., *Effect of conjugation methodology, carrier protein, and adjuvants on the immune response to Staphylococcus aureus capsular polysaccharides*, Vaccine, vol. 13, No. 14, pp. 1288-1293 (1995).
Henderson, *Bioconjugate Techniques*, Academic Press, XP-002473633; pp. 34, 187-188, 218-220, 228-248 (1996).

* cited by examiner

*Primary Examiner* — S. Devi
(74) *Attorney, Agent, or Firm* — Jason C. Fedon; William T. Han

(57) ABSTRACT

The present application describes a process for conjugating a PNAG which is less than 40% N-acetylated to a carrier protein.

8 Claims, No Drawings

CONJUGATION PROCESS FOR PNAG AND A CARRIER PROTEIN

This application is filed pursuant to 35 U.S.C. §371 as a United States National Phase Application of International Patent Application Serial No. PCT/EP2007/053060 filed Mar. 29, 2007, which claims priority from Great Britain Applications No. 0606416.6 and 0606417.4 filed in the United Kingdom on Mar. 30, 2006, and from U.S. Applications No. 60/787,249 and 60/787,587 filed in the United States on Mar. 30, 2006, the contents of which are incorporated herein by reference.

The present invention relates to the field of conjugation and provides a method for conjugating PNAG to a carrier protein. The PNAG-carrier protein conjugate may be further formulated to provide a vaccine. The invention also encompasses a PNAG-carrier protein conjugate, a vaccine comprising a PNAG-carrier protein conjugate and their use in therapy.

The number of both community acquired and hospital acquired infections have increased over recent years with the increased use of intravascular devices. Hospital acquired (nosocomial) infections are a major cause of morbidity and mortality, more particularly in the US, where they affect more than 2 million patients annually. Following various studies, about 6 percent of the US patients will acquire an infection during their stay in hospital. The economic burden in the USA was estimated to be more than $4.5 billion in 1992 (Emori and Gaynes, 1993, Clin. Microbiol. Rev. 6; 428). The most frequent infections are urinary tract infections (UTI-33% of the infections), followed by pneumonia (15.5%), surgical site infections (14.8%) and primary bloodstream infections (13%) Emori and Gaynes, 1993, Clin. Microbiol. Rev. 6; 428).

*Staphylococcus aureus*, Coagulase-negative Staphylococci (mostly *Staphylococcus epidermidis*), enterococcus spp, *Escherichia coli* and *Pseudomonas aeruginosa* are the major nosocomial pathogens. Although those pathogens almost cause the same number of infections, the severity of the disorders they can produce combined with the frequency of antibiotic resistant isolates balance this ranking towards *S. aureus* and *S. epidermidis* as being the most significant nosocomial pathogens.

*Staphylococcus aureus* is the most common cause of nosocomial infections with a significant morbidity and mortality (Romero-Vivas et al 1995, Infect. Dis. 21; 1417). It is the cause of some cases of osteomyelitis, endocarditis, septic arthritis, pneumonia, abscesses and toxic shock syndrome.

*S. epidermidis* is a normal skin commensal which is also an important opportunistic pathogen responsible for infections of implanted medical devices and infections at sites of surgery. Medical devices infected by *S. epidermidis* include cardiac pacemakers, cerebrospinal fluid shunts, continuous ambulatory peritoneal dialysis catheters, orthopaedic devices and prosthetic heart valves.

*S. aureus* and *S. epidermidis* infections are treated with antibiotics, with penicillin being the drug of choice whereas vancomycin is used for methicillin resistant isolates. The percentage of staphylococcal strains exhibiting wide-spectrum resistance to antibiotics has become increasingly prevalent since the 1980's (Panlilo et al 1992, Infect. Control. Hosp. Epidemiol. 13; 582), posing a threat for effective antimicrobial therapy. In addition, the recent emergence of vancomycin resistant *S. aureus* strain has aroused fear that methicillin resistant *S. aureus* strains will emerge and spread for which no effective therapy is available.

An alternative approach of using antibodies against staphylococcal antigens in passive immunotherapy has been investigated. Therapy involving administration of polyclonal antisera are under development (WO 00/15238, WO 00/12132) as well as treatment with a monoclonal antibody against lipoteichoic acid (WO 98/57994).

An alternative approach would be use of active vaccination to generate an immune response against staphylococci. Several candidates for inclusion as vaccine components have been identified. These include poly N-acetylated glucosamine (PNAG) which is a surface polysaccharide found in staphylococci for instance *S. aureus* and *S. epidermeridis*. Particularly where this antigen is in a deacetylated form (dP-NAG), it has been shown to generate an opsonic immune response (WO 04/43405). WO 04/43405 disclosed the conjugation of PNAG to a carrier protein using the organic cyanylating agent 1-cyano-4-dimethylaminopyridinium tetrafluoroborate (CDAP) and the conjugation of dPNAG to a carrier protein by activation of the carrier protein with glutaraldehyde followed by reductive amination.

The CDAP conjugation described is not appropriate for use with dPNAG because activated dPNAG can react with NH2 groups on dPNAG so that there is a risk of cross-linking the dPNAG if CDAP chemistry is used. The method described for the conjugation of dPNAG has the disadvantage of using glutaraldehyde treatment as a first step to introduce aldehyde groups onto the carrier protein. The glutaraldehyde treatment tends not to be reliably reproducible since different batches of glutaraldehyde can lead to varying results. Glutaraldehyde treatment can also lead to crosslinking of the carrier protein.

Further methods of conjugating deacetylated PNAG to a carrier protein, avoiding the use of glutaraldehyde are required to maximise the usefulness of PNAG as a vaccine component.

According to a first aspect of the invention there is provided a process for conjugating a PNAG which is less than 40% N-acetylated to a carrier protein comprising the steps of;

a) activating the PNAG by adding a linker comprising a maleimide group to form an activated PNAG;
b) activating the carrier protein by adding a linker comprising a sulphydryl group to form an activated carrier protein; and
c) reacting the activated PNAG and the activated carrier protein to form a PNAG-carrier protein conjugate; or
a) activating the PNAG by adding a linker comprising a sulphydryl group to form an activated PNAG;
b) activating the carrier protein by adding a linker comprising a maleimide group to form an activated carrier protein; and
c) reacting the activated PNAG and the activated carrier protein to form a PNAG-carrier protein conjugate; or
a) activating the PNAG by adding a linker comprising a sulphydryl group to form an activated PNAG;
b) activating the carrier protein by adding a linker comprising a sulphydryl group to form an activated carrier protein; and
c) reacting the activated PNAG and the activated carrier protein to form a PNAG-carrier protein conjugate.

According to a second aspect of the invention, there is provided a process for making a vaccine comprising carrying out the conjugation process of the invention and adding a further step of combining the PNAG-carrier protein conjugate with a pharmaceutically acceptable excipient.

According to a third aspect of the invention, there is provided a PNAG-carrier protein conjugate obtainable by the process of the invention.

According to a fourth aspect of the invention there is provided a PNAG-carrier protein conjugate wherein the PNAG is less than 40% N-acetylated and the PNAG and the carrier protein are joined by a linker comprising either a maleimide group bonded to a sulphur atom or a sulphur atom bonded to a sulphur atom.

According to a fifth aspect of the invention there is provided an activated PNAG having less than 40% N-acetylation wherein the PNAG is covalently bonded to a linker comprising a maleimide group.

According to a sixth aspect of the invention, there is provided a vaccine comprising a PNAG-carrier protein conjugate obtainable by the process of the invention.

According to a further aspect of the invention, there is provided a PNAG-carrier protein conjugate of the invention for use in the treatment or prevention of staphylococcal disease.

According to a further aspect of the invention, there is provided a use of the PNAG—carrier protein conjugate of the invention in the preparation of a vaccine for treatment or prevention of staphylococcal disease.

According to a further aspect of the invention, there is provided a method of treating or preventing staphylococcal disease comprising the step of administering the vaccine of the invention to a human or animal patient.

DETAILED DESCRIPTION

The present invention describes a process for conjugating a PNAG which is less than 40, 35, 30, 20, 15, 10 or 5% N-acetylated to a carrier protein comprising the steps of;
  a) activating the PNAG by adding a linker comprising a maleimide group to form an activated PNAG;
  b) activating the carrier protein by adding a linker comprising a sulphydryl group to form an activated carrier protein; and
  c) reacting the activated PNAG and the activated carrier protein to form a PNAG-carrier protein conjugate.

As an independent aspect of the invention, the present invention describes a process for conjugating a PNAG which is less than 40, 35, 30, 20, 15, 10 or 5% N-acetylated to a carrier protein comprising the steps of;
  a) activating the carrier protein by adding a linker comprising a maleimide group to form an activated carrier protein;
  b) activating the PNAG by adding a linker comprising a sulphydryl group to form an activated PNAG; and
  c) reacting the activated PNAG and the activated carrier protein to form a PNAG-carrier protein conjugate.

As an independent aspect of the invention, the present invention describes a process for conjugating a PNAG which is less than 40, 35, 30, 20, 15, 10 or 5% N-acetylated to a carrier protein comprising the steps of;
  a) activating the carrier protein by adding a linker comprising a sulphydryl group to form an activated carrier protein;
  b) activating the PNAG by adding a linker comprising a sulphydryl group to form an activated PNAG; and
  c) reacting the activated PNAG and the activated carrier protein to form a PNAG-carrier protein conjugate.

The term PNAG comprises both dPNAG and PNAG. The PNAG is less than 40, 35, 30, 25, 20, 15, 10, 5, 2 or 1% N-acetylated so that it is predominantly in the deacetylated form. De-acetylated epitopes of PNAG can elicit antibodies that are capable of mediating opsonic killing of Gram positive bacteria, for example S. aureus and/or S. epidermidis. In an embodiment, the PNAG is not O-succinylated or is O-succinylated on less than 25, 20, 15, 10, 5, 2, 1 or 0.1% of residues.

PNAG may be of different sizes varying from over 400 kDa to between 75 and 400 kDa to between 10 and 75 kDa to oligosaccharides composed of up to 30 repeat units. Any size of PNAG polysaccharide or oligosaccharide may be use in the process of the invention for example, over 40, 50, 60, 80, 100 or 200 kDa or between 40-400 kDa, 50-350 kDa, 40-300 kDa, 60-300 kDa, 50-250 kDa, 60-200 kDa, 70-150 kDa or 80-120 kDa. Sizing may be achieved by any method known in the art, for instance by microfluidisation, ultrasonic irradiation or by chemical cleavage (WO 03/53462, EP497524, EP497525).

In an embodiment, PNAG is deacetylated to form dPNAG by chemically treating the native polysaccharide. For example, the native PNAG is treated with a basic solution such that the pH rises to above 10. For instance the PNAG is treated with 0.1-5M, 0.2-4M, 0.3-3M, 0.5-2M, 0.75-1.5M, about 1.5M, about 2M, about 5M or about 1M NaOH, KOH or $NH_4OH$. Treatment is for at least 10 or 30 minutes, or 1, 2, 3, 4, 5, 10, 15, 20 or 24 hours at a temperature of 20-100, 25-80, 30-60 or 30-50 or 35-45° C. dPNAG may be prepared as described in WO 04/43405.

Conjugation is the covalent coupling of the PNAG to a carrier protein. It may be direct or indirect, incorporating a further crosslinking compound which is reactive with the maleimide and sulphydryl groups of the activated PNAG and activated carrier protein.

The term linker refers to the molecule which covalently links the PNAG and the carrier protein in the completed conjugate. The linker may originate from the covalent bonding of two molecules which were used in the conjugation reaction. Alternatively, the linker may derive from a single molecule used in the conjugation reaction (for example where a sulphydryl group from a cysteine residue of the carrier protein reacts with a maleimide or sulphydryl group on the activated PNAG).

In an aspect of the first embodiment, the linker comprising a maleimide group is attached to an amine group on PNAG during step a).

In an aspect of the second embodiment, the linker comprising a maleimide group is attached to an amine group on the carrier protein during step b).

In an embodiment, the linker comprises a maleimide group which is derived from a compound selected from the group consisting of BMPS, EMCS, GMBS, MBS, LC-SMCC, SMCC, SMPB, SMPH, Sulfo-EMCS, Sulfo-MBS, Sulfo-SMCC, Sulfo-GMBS and Sulfo-SMPB.

In an embodiment, the linker comprising a maleimide group has a spacer length of 5-10, 6-8, 10-20, 12-17, about 7, about 10 or about 15 Angstroms.

In an embodiment during step a) the weight/weight ratio of PNAG to the linker comprising a maleimide group is 1:5-5:1, 1:2-2:1, 1:1.5-1.5:1 or approximately 1:1.

By approximately or about, it is meant that the figure should be within 10% of that provided.

In an embodiment, the step of activating either PNAG or the carrier protein by adding a linker comprising a maleimide group is carried out at a pH of 6.0-8.0, 6.5-7.5 or approximately 7.0.

In an embodiment, the linker comprising a sulphydryl group is attached to an amine group on the carrier protein during step a) or b). In an embodiment, the linker comprising a sulphydryl group is attached to an amine group on the PNAG during step b).

In an embodiment, the linker comprises a sulphydryl group which is derived or derivable from a compound selected from the group consisting of SPDP, LC-SPDP, SMPT, LC-SMPT, Sulfo-SPDP, Sulfo-SMPT, Sulfo-LC-SMPT, Sulfo-LC-SPDP and N-acetyl homocysteine thiolactone.

In an embodiment, the linker comprising a sulphydryl group has a spacer length of 4-25, 5-10, 6-8, 10-20, 13-17, 5-20, about 7 or about 15 Angstroms.

In an embodiment wherein PNAG is activated by adding a first linker and the carrier protein is activated by adding a second linker, the first and second linkers are optionally derived or derivable from GMBS and SPDP; GMBS and LC-SPDP, Sulpho-GMBS and SPDP, Sulpho-GMBS and LC-SPDP, SPDP and GMBS; SPDP and Sulpho-GMBS; LC-SPDP and GMBS; or LC-SPDP and sulpho-GMBS respectively.

In an embodiment wherein PNAG is activated by adding a first linker comprising a sulphydryl group and the carrier protein is activated by adding a second linker comprising a sulphydryl group, the first and second linker may be the same or different. For example, the first and second linkers may be derived or derivable from SPDP and SPDP; SPDP and LC-SPDP; SPDP and SMPT; SDPD and LC-SMPT, LC-SPDP and SDPD, LC-SPDP and LC-SPDP; LC-SPDP and SMPT, LC-SDPD and LC-SMPT; SMPT and SPDP; SMPT and LC-SPDP; SMPT and SMPT; SMPT and LC-SMPT; LC-SMPT and SPDP; LC-SMPT and LC-SDPD, LC-SMPT and SMPT or LC-SMPT and LC-SMPT respectively.

In an embodiment, during the step of activating the carrier protein by adding a linker comprising a sulphydryl group, the weight/weight ratio of the carrier protein to the linker comprising a sulphydryl group is 100:1-1:1, 50:1-2:1, 20:1-3:1, 15:1-5:1 or approximately 10:1.

In an embodiment the step of activating the carrier protein by adding a linker comprising a sulphydryl group is carried out at a pH of 7.0-9.0, 7.5-8.5 or approximately 8.0.

In an embodiment, during step c) the weight/weight ratio of the activated PNAG to the activated carrier protein is 10:1-1:10, 9:1-1:5, 8:1-1:2, 7:1-1:1, 5:1-1:1 or approximately 2:1.

In an embodiment step c) is carried out at a pH of 6.0-9.0, 6.0-8.0, 6.5-7.5 or approximately 7.0.

In an embodiment, the length of the linker between the PNAG and carrier protein after completion of step c) is 5-40, 10-30, 12-25, 10-15, 15-25, 20-25, 20-30, 25-30, 30-40, about 14, about 23, about 28 or about 30 Angstroms.

In an embodiment, the process of the invention comprises a further step d) of blocking excess maleimide groups with cysteine.

In an embodiment, the carrier protein is selected from the group consisting of tetanus toxoid, diphtheria toxoid, CRM197, rEPA, protein D, SitC/MntC/saliva binding protein, EbhA, EbhB, Elastin binding protein (EbpS), EFB (FIB), SBI, ClfA, SdrC, SdrG, SdrH, Lipase GehD, SasA, FnbA, FnbB, Cna, ClfB, FbpA, Npase, IsaA/P isA, SsaA, EPB, SSP-1, SSP-2, HBP, Vitronectin binding protein, fibrinogen binding protein, coagulase, Fig, MAP, IsdA, IsdB, HarA, SitC, alpha toxin (Hla), alpha toxin H35R mutant, MRPII and autolysin, or fragments thereof.

Examples of carrier proteins which are currently used for coupling to polysaccharide or oligosaccharide immunogens include the Diphtheria and Tetanus toxoids (DT, DT CRM197 and TT), Keyhole Limpet Haemocyanin (KLH), *Pseudomonas aeruginosa* exoprotein A (rEPA) and the purified protein derivative of Tuberculin (PPD), protein D from *Haemophilus influenzae*, pneumolysin or fragments of any of the above. Fragments suitable for use include fragments encompassing T-helper epitopes. In particular protein D fragment will preferably contain the N-terminal 1/3 of the protein. Protein D is an IgD-binding protein from *Haemophilus influenzae* (EP 0 594 610 B1).

An alternative carrier protein to use in the process of the invention is a single staphylococcal protein or fragment thereof or a fusion protein comprising at least or exactly 1, 2, 3 or 4 or more of the staphylococcal proteins, for example selected from those disclosed below or fragments thereof.

In an embodiment, alpha toxin is used as a carrier protein. The native form may be conjugated to a polysaccharide since the process of conjugation highly reduces or removes toxicity. Preferably a genetically detoxified alpha toxin such as the His35Leu or His 35 Arg variants are used as carriers since residual toxicity is lower. Alternatively the alpha toxin is chemically detoxified by treatment with a cross-linking reagent, formaldehyde or glutaraldehyde. A genetically detoxified alpha toxin is optionally chemically detoxified, preferably by treatment with a cross-linking reagent, formaldehyde or glutaraldehyde to further reduce toxicity.

In an embodiment, the process of the invention comprises a further step of combining the PNAG-carrier protein conjugate with a pharmaceutically acceptable excipient which optionally comprises an adjuvant.

Suitable adjuvants include an aluminum salt such as aluminum hydroxide gel (alum) or aluminium phosphate, but may also be a salt of calcium, magnesium, iron or zinc, or may be an insoluble suspension of acylated tyrosine, or acylated sugars, cationically or anionically derivatized polysaccharides, or polyphosphazenes.

In an embodiment, the adjuvant is a preferential inducer of either a TH1 or a TH2 type of response. High levels of Th1-type cytokines tend to favor the induction of cell mediated immune responses to a given antigen, whilst high levels of Th2-type cytokines tend to favour the induction of humoral immune responses to the antigen.

It is important to remember that the distinction of Th1 and Th2-type immune response is not absolute. In reality an individual will support an immune response which is described as being predominantly Th1 or predominantly Th2. However, it is often convenient to consider the families of cytokines in terms of that described in murine CD4 +ve T cell clones by Mosmann and Coffman (Mosmann, T. R. and Coffman, R. L. (1989) TH1 and TH2 cells: different patterns of lymphokine secretion lead to different functional properties. Annual Review of Immunology, 7, p145-173). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of Il-4, IL-5, IL-6, IL-10. Suitable adjuvant systems which promote a predominantly Th1 response include: Monophosphoryl lipid A or a derivative thereof, particularly 3-de-O-acylated monophosphoryl lipid A (3D-MPL) (for its preparation see GB 2220211 A); and a combination of monophosphoryl lipid A, preferably 3-de-O-acylated monophosphoryl lipid A, together with either an aluminium salt (for instance aluminium phosphate or aluminium hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen [Thoelen et al. Vaccine (1998) 16:708-14; EP 689454-B1].

An enhanced system involves the combination of a monophosphoryl lipid A and a saponin derivative, particularly the combination of QS21 and 3D-MPL as disclosed in WO 94/00153, or a less reactogenic composition where the QS21 is quenched with cholesterol as disclosed in WO 96/33739. A particularly potent adjuvant formulation involving QS21, 3D-MPL and tocopherol in an oil in water emulsion is described in WO 95/17210. Optionally the vaccine additionally comprises a saponin, more preferably QS21. The formulation may also comprise an oil in water emulsion and tocopherol (WO 95/17210). The present invention also provides a method for producing a vaccine formulation comprising mixing a PNAG conjugate of the present invention together with a pharmaceutically acceptable excipient, such as 3D-MPL. Unmethylated CpG containing oligonucleotides (WO 96/02555) are also preferential inducers of a TH1 response and are suitable for use in the present invention. The adjuvant optionally forms a liposome structure or an ISCOM structure.

The ratio of QS21: sterol will typically be in the order of 1:100 to 1:1 weight to weight. In an embodiment excess sterol is present, the ratio of QS21: sterol being at least 1:2 w/w. Typically for human administration QS21 and sterol will be present in a vaccine in the range of about 1 µg to about 100 µg, or about 10 µg to about 50 µg per dose.

The liposomes optionally contain a neutral lipid, for example phosphatidylcholine, which is optionally non-crystalline at room temperature, for example eggyolk phosphatidylcholine, dioleoyl phosphatidylcholine or dilauryl phosphatidylcholine. The liposomes may also contain a charged lipid which increases the stability of the lipsome-QS21 structure for liposomes composed of saturated lipids. In these cases the amount of charged lipid is optionally 1-20% w/w, optionally 5-10%. The ratio of sterol to phospholipid is 1-50% (mol/mol), optionally 20-25%.

In an embodiment, the adjuvant contains MPL (3-deacylated mono-phosphoryl lipid A, also known as 3D-MPL). 3D-MPL is known from GB 2 220 211 (Ribi) as a mixture of 3 types of De-O-acylated monophosphoryl lipid A with 4, 5 or 6 acylated chains and is manufactured by Ribi Immunochem, Montana (WO 92/116556).

In an embodiment, the adjuvant contains liposomes initially prepared without MPL, to which MPL is then added, optionally as 100 nm particles. The MPL is therefore not contained within the vesicle membrane (known as MPL out). Compositions where the MPL is contained within the vesicle membrane (known as MPL in) also form an aspect of the invention. The antigen can be contained within the vesicle membrane or contained outside the vesicle membrane. Optionally soluble antigens are outside and hydrophobic or lipidated antigens are either contained inside or outside the membrane.

In an embodiment, the process of the invention comprises a further step of combining the PNAG-carrier protein conjugate with an additional antigen(s). In an embodiment, 1, 2, 3, 4, 5, 6, 7, 8, 9, or 10 additional antigens are added. In an embodiment, the additional antigen(s) comprise a bacterial polysaccharide or oligosaccharide.

Examples of such antigens include capsular polysaccharides or oligosaccharides from type 5 and/or type 8 *Staphylococcus aureus*.

Most strains of *S. aureus* that cause infection in man contain either Type 5 or Type 8 polysaccharides. Approximately 60% of human strains are Type 8 and approximately 30% are Type 5. The structures of Type 5 and Type 8 capsular polysaccharide antigens are described in Moreau et al Carbohydrate Res. 201; 285 (1990) and Fournier et al Infect. Immun. 45; 87 (1984). Both have FucNAcp in their repeat unit as well as ManNAcA which can be used to introduce a sulfhydryl group.

Recently (Jones Carbohydrate Research 340, 1097-1106 (2005)) NMR spectroscopy revised the structures of these capsular polysaccharides to:

Type 5
→4)-β-D-ManNAcA-(1→4)-α-L-FucNAc(3OAc)-(1→3)-β-D-FucNAc-(1→

Type 8
→3)-β-D-ManNAcA(4OAc)-(1→3)-α-L-FucNAc(1→3)-α-D-FucNAc(1→

Polysaccharides may be extracted from the appropriate strain of *S. aureus* using methods well known to the skilled man, for instance as described in U.S. Pat. No. 6,294,177. For example, ATCC 12902 is a Type 5 *S. aureus* strain and ATCC 12605 is a Type 8 *S. aureus* strain.

Polysaccharides are of native size or alternatively may be sized, for instance by microfluidisation, ultrasonic irradiation or by chemical treatment. Oligosaccharides may also be used in the process of the invention.

The type 5 and 8 polysaccharides used in the process of the invention are optionally conjugated (for example using the method disclosed in any one of U.S. Pat. No. 4,372,945, U.S. Pat. No. 4,474,757, U.S. Pat. No. 4,356,170, U.S. Pat. No. 4,830,852 or WO 95/08348) to a carrier protein which may be any of those described above or are alternatively unconjugated.

In an embodiment, the additional antigen(s) comprises the 336 antigen from *S. aureus* described in U.S. Pat. No. 6,294,177.

In an embodiment, the 336 antigen is a polysaccharide which is of native size or alternatively may be sized, for instance by microfluidisation, ultrasonic irradiation or by chemical treatment. Oligosaccharides derived from the 336 antigen may also be used. The 336 antigen is preferably conjugated to a carrier protein using any known conjugation method, for example those described in U.S. Pat. No. 4,372,945, U.S. Pat. No. 4,474,757, U.S. Pat. No. 4,356,170, U.S. Pat. No. 4,830,852 or WO 95/08348 or is alternatively unconjugated.

Strains ATCC-31432, SE-360 and SE-10 of *S. epidermidis* are characteristic of three different capsular types, I, II and III respectively (Ichiman and Yoshida 1981, J. Appl. Bacteriol. 51; 229). Capsular polysaccharides extracted from each serotype of *S. epidermidis* constitute Type I, II and III polysaccharides. Polysaccharides may be extracted by several methods including the method described in U.S. Pat. No. 4,197,290 or as described in Ichiman et al 1991, J. Appl. Bacteriol. 71; 176.

In one embodiment of the invention, the additional antigen(s) comprises type I and/or II and/or III polysaccharides or oligosaccharides from *S. epidermidis*. Polysaccharides are of native size or alternatively may be sized, for instance by microfluidisation, ultrasonic irradiation or chemical cleavage. The additional antigen(s) may also include oligosaccharides extracted from *S. epidermidis* strains. These polysaccharides or oligosaccharides are unconjugated or are preferably conjugated using any known method of conjugation for example those described in U.S. Pat. No. 4,372,945, U.S. Pat. No. 4,474,757, U.S. Pat. No. 4,356,170, U.S. Pat. No. 4,830,852, or WO 95/08348.

In an embodiment, the additional antigen(s) comprise a staphylococcal protein or fragment thereof. For example, a protein from *S. aureus* or *S. epidermidis*. Some embodiments of the invention contain proteins from both *S. aureus* and *S. epidermidis*. The additional antigen(s) is for example an isolated protein which comprises an amino acid sequence which has at least 85% identity, preferably at least 90% identity, more preferably at least 95% identity, most preferably at least 97-99% or exact identity, to that of any sequence of figure 1.

Where a protein is specifically mentioned herein, it may be a reference to a native or recombinant, full-length protein or optionally a mature protein in which any signal sequence has been removed. The protein may be isolated directly from the staphylococcal strain or produced by recombinant DNA techniques. Immunogenic fragments of the protein may be incorporated into the immunogenic composition of the invention. These are fragments comprising at least 10 amino acids, at least 20 amino acids, at least 30 amino acids, at least 40 amino acids, at least 50 amino acids, or at least 100 amino acids, taken contiguously from the amino acid sequence of the protein. In addition, such immunogenic fragments are typically immunologically reactive with antibodies generated against the Staphylococcal proteins or with antibodies generated by infection of a mammalian host with Staphylococci or contain T cell epitopes. Immunogenic fragments also includes fragments that when administered at an effective dose, (either alone or as a hapten bound to a carrier), elicit a protective immune response against Staphylococcal infection, optionally it is protective against S. aureus and/or S. epidermidis infection. Such an immunogenic fragment may include, for example, the protein lacking an N-terminal leader sequence, and/or a transmembrane domain and/or a C-terminal anchor domain. In an embodiment the immunogenic fragment used in the process of the invention comprises substantially all of the extracellular domain of a protein which has at least 85% identity, at least 90% identity, at least 95% identity, or at least 97-99% identity, to that a sequence selected from Figure 1 over the entire length of the fragment sequence.

In an embodiment, the additional antigen(s) may contain fusion proteins of Staphylococcal proteins, or fragments of staphylococcal proteins. Such fusion proteins may be made recombinantly and may comprise one portion of at least 2, 3, 4, 5 or 6 staphylococcal proteins. Alternatively, a fusion protein may comprise multiple portions of at least 2, 3, 4 or 5 staphylococcal proteins. These may combine different Staphylococcal proteins or fragments thereof in the same protein. Alternatively, the invention also includes individual fusion proteins of Staphylococcal proteins or fragments thereof, as a fusion protein with heterologous sequences such as a provider of T-cell epitopes or purification tags, for example: 8-galactosidase, glutathione-5-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, CRM197.

The additional antigen(s) optionally comprises a staphylococcal extracellular component binding protein or a staphylococcal transporter protein or a staphylococcal toxin or regulator of virulence. The additional antigen(s) optionally comprises at least or exactly 1, 2, 3, 4, 5 or 6 staphylococcal proteins. Examples of extracellular component binding proteins are laminin receptor, SitC/MntC/saliva binding protein, EbhA, EbhB, Elastin binding protein (EbpS), EFB (FIB), SBI, autolysin, ClfA, SdrC, SdrG, SdrH, Lipase GehD, SasA, FnbA, FnbB, Cna, ClfB, FbpA, Npase, IsaA/P isA, SsaA, EPB, SSP-1, SSP-2, HBP, Vitronectin binding protein, fibrinogen binding protein, coagulase, Fig and MAP. Examples of staphylococcal transporter proteins are Immunodominant ABC transporter, IsdA, IsdB, Mg2+ transporter, SitC and Ni ABC transporter. Examples of a staphylococcal toxin or regulator of virulence are alpha toxin (Hla), alpha toxin H35R mutant and RNA III activating protein (RAP).

A further aspect of the invention is a PNAG-carrier protein conjugate obtainable or obtained by the process of the invention.

The PNAG-carrier protein conjugate of the invention comprises PNAG which is less than 40% N-acetylated and the PNAG and the carrier protein are joined by a linker comprising a maleimide group bonded to a sulphur atom.

In an embodiment, the maleimide group is positioned between the PNAG and the sulphur atom. Alternatively the maleimide group is positioned between the carrier protein and the sulphur atom.

In an embodiment, the PNAG-carrier protein conjugate has the structure:

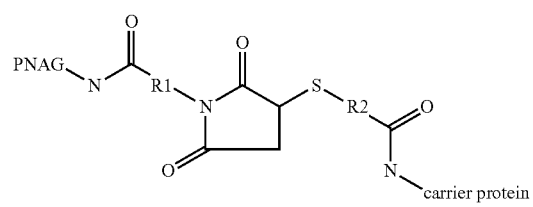

wherein R1 and R2 are independently selected from an aromatic or aliphatic chain, optionally substituted, or a bond. In an embodiment R1 is a C1-C6 alkyl, a C2-C5 alkyl, a C3-C4 alkyl, a C2 alkyl, a C3 alkyl, a C4 alkyl or a C5 alkyl. In an embodiment R2 is a C1-C6 alkyl, a C2-C5 alkyl, a C3-C4 alkyl, a C2 alkyl, a C3 alkyl, a C4 alkyl or a C5 alkyl.

In an embodiment, the PNAG-carrier protein conjugate of in the invention has the structure:

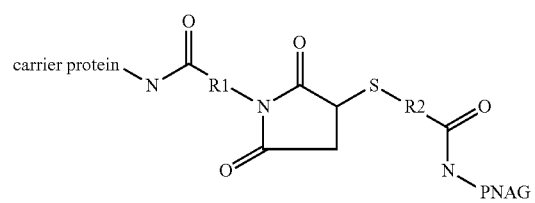

wherein R1 and R2 are independently selected from an aromatic or aliphatic chain, optionally substituted, or a bond. In an embodiment R1 is a C1-C6 alkyl, a C2-C5 alkyl, a C3-C4 alkyl a C2 alkyl, a C3 alkyl, a C4 alkyl or a C5 alkyl. In an embodiment R2 is a C1-C6 alkyl, a C2-C5 alkyl, a C3-C4 alkyl, a C2 alkyl, a C3 alkyl, a C4 alkyl or a C5 alkyl.

A further aspect of the invention is a PNAG-carrier protein conjugate wherein the PNAG is less than 40% N-acetylated and the PNAG and the carrier protein are joined by a linker comprising a sulphur atom bonded to a sulphur atom.

In an embodiment the PNAG-carrier protein conjugate has the structure:

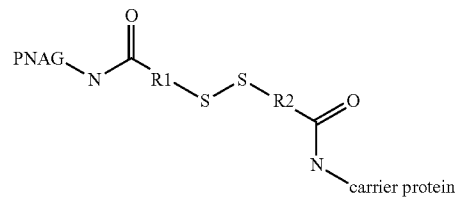

wherein R1 and R2 are independently selected from an aromatic or aliphatic chain, optionally substituted, or a bond. In an embodiment R1 is a C1-C6 alkyl, a C2-C5 alkyl, a C3-C4 alkyl, a C2 alkyl, a C3 alkyl, a C4 alkyl or a C5 alkyl. In an embodiment R2 is a C1-C6 alkyl, a C2-C5 alkyl, a C3-C4 alkyl, a C2 alkyl, a C3 alkyl, a C4 alkyl or a C5 alkyl.

In an embodiment the PNAG-carrier protein conjugate has the structure:

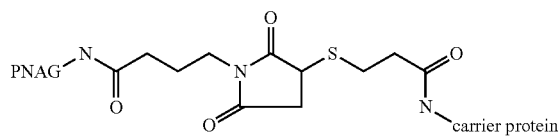

A further aspect of the invention is an activated PNAG having less than 40% N-acetylation wherein the PNAG is covalently bonded to a linker comprising a maleimide group. In an embodiment, the maleimide group is derived from or derivable from a compound selected from the group consisting of BMPS, EMCS, GMBS, MBS, LC-SMCC, SMCC, SMPB, SMPH, Sulfo-EMCS, Sulfo-MBS, Sulfo-SMCC, Sulfo-GMBS and Sulfo-SMPB.

In an embodiment, the activated PNAG has the structure:

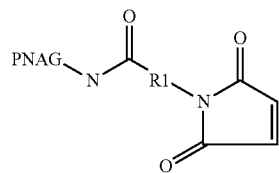

wherein R1 is selected from an aromatic or aliphatic chain, optionally substituted, or a bond. In an embodiment R1 is a C1-C6 alkyl, a C2-C5 alkyl, a C3-C4 alkyl, a C2 alkyl, a C3 alkyl, a C4 alkyl or a C5 alkyl. In an embodiment, the linker is 5-40, 10-30, 12-25, 10-15, 15-25, 20-25, 20-30, 25-30, 30-40, about 14, about 23, about 28 or about 30 Angstroms long.

The PNAG-carrier protein conjugates and vaccine preparations made by the process of the present invention may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts. Although the vaccine of the invention may be administered as a single dose, components thereof may also be co-administered together at the same time or at different times. For co-administration, the optional Th1 adjuvant may be present in any or all of the different administrations, however it is preferred if it is present in combination with the bacterial protein component of the vaccine. In addition to a single route of administration, 2 different routes of administration may be used. For example, polysaccharides may be administered IM (or ID) and bacterial proteins may be administered IN (or ID). In addition, the vaccines of the invention may be administered IM for priming doses and IN for booster doses.

The amount of conjugate antigen in each vaccine dose is selected as an amount which induces an immunoprotective response without significant, adverse side effects in typical vaccines. Such amount will vary depending upon which specific immunogen is employed and how it is presented. Generally, it is expected that each dose will comprise 0.1-100 μg of polysaccharide, preferably 0.1-50 μg for polysaccharide conjugates, preferably 0.1-10 μg, more preferably 1-10 μg, of which 1 to 5 μg is a more preferable range.

The content of protein antigens in the vaccine will typically be in the range 1-100 μg, preferably 5-50 μg, most typically in the range 5-25 μg. Following an initial vaccination, subjects may receive one or several booster immunizations adequately spaced.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

The vaccines of the present invention may be stored in solution or lyophilized. Preferably the solution is lyophilized in the presence of a sugar such as sucrose, trehalose or lactose. It is still further preferable that they are lyophilized and extemporaneously reconstituted prior to use. Lyophilizing may result in a more stable composition (vaccine) and may possibly lead to higher antibody titers in the presence of 3D-MPL and in the absence of an aluminium based adjuvant.

The terms "comprising", "comprise" and "comprises" herein are intended by the inventors to be optionally substitutable with the terms "consisting of", "consist of" and "consists of", respectively, in every instance.

All references or patent applications cited within this patent specification are incorporated by reference herein.

In order that this invention may be better understood, the following examples are set forth. These examples are for purposes of illustration only, and are not to be construed as limiting the scope of the invention in any manner.

EXAMPLES

Example 1

Preparation of a PNAG-TT Conjugate dPNAG was prepared as described in WO 04/43405. The dPNAG was further purified on a SUPEROSE™ 6 column.

dPNAG Activation dPNAG (12 mg) was dissolved in 300 μl 5M HCl+300 μl 5M NaOH+1700 μl of 1×PBS pH 7.0. and the pH adjusted to 7.0. The sample was filtrated through a 0.22 μm filter and the pH adjusted again to 7.0. 12 mg of GMBS was added in 200 μl DMSO and the sample stirred slowly for 2 hours at room temperature in the dark. The pH was maintained at 7.0 with 0.5M NaOH. Excess GMBS was removed with a desalting column (PD10 column) equilibrated with 1×PBS, 10 mM EDTA pH 7.0 buffer and sample was concentrated to 0.6 ml using a CENTRICON® 10 KDa MWCO concentrating device.

TT Activation

Tetanus toxoid (TT) (6.5 mg; 195 μl stock solution) was added to 1105 μl 1×PBS containing 10 mM EDTA, pH8.0. 130 μl of SPDP (6.2 mg/ml in DMSO) was added to the protein solution and stirred slowly for 1 hour at room temperature in the dark. The pH was maintained at 8.0 using 0.5M NaOH. Excess SPDP was removed using a desalting column (PD10 column) equilibrated with 1×PBS, 10 mM EDTA pH 8.0 buffer and the sample was concentrated to 1.3 ml using a CENTRICON® 10 KDa MWCO. 0.65 ml of DTT (23 mg/ml in 1×PBS, 10 mM EDTA pH 8.0 buffer) was added to 1.3 ml of the SPDP-activated TT. The sample was incubated for 30 minutes at room temperature in the dark. The pH was maintained at 8.0 using 0.5M NaOH. Excess DTT was removed with a desalting column (PD10 column) equilibrated with 1×PBS, 10 mM EDTA pH 7.0 buffer and the sample was concentrated to 0.6 ml using a CENTRICON® 10 KDa MWCO concentrating device.

GMBS-activated dPNAG (0.6 ml)+SH-SPDP-TT (0.6 ml) were mixed and stirred slowly for 2 hours at room temperature in the dark. Excess maleimides were blocked with 3 mg of cysteine in 100 µl of 1×PBS, 10 mM EDTA pH 7.0 for 30 minutes. The sample was chromatographed over a SUPEROSE™ 6 column at 1 ml/min with 1×PBS, 10 mM EDTA pH 7.0 as running buffer. Fractions were tested for protein using a Bradford assay. Fractions containing conjugate were pooled and concentrated to 25 ml using SPECTRA/GELT™ adsorbent. The final conjugate was tested for polysaccharide and protein composition.

dPNAG-TT Composition
dPNAG: 153.37 µg/ml (46.3%)
TT: 178.06 µg/ml (53.7%)

Example 2

Activation and Coupling of dPNAG dPNAG-TT Conjugates

The following conjugates were produced using the approaches described herebelow:
dPNAG-TT010: dPNAG-S-GMBS+DTT treated TT-LC-SPDP
dPNAG-TT011: dPNAG-S-GMBS+DTT treated TT-LC-SPDP
dPNAG-TT012: dPNAG-S-GMBS+DTT treated TT-SPDP
dPNAG-TT014: dPNAG-SPDP+DTT treated TT-SPDP
dPNAG-TT017: DTT treated dPNAG-SPDP+TT-LC-SPDP
dPNAG-TT019: dPNAG-S-GMBS+DTT treated TT-SPDP
dPNAG-TT020: dPNAG-S-GMBS+DTT treated TT-SPDP dPNAG 1 g of PNAG was dissolved in 5N HCl at a concentration of 20 mg/ml and was incubated for 1 hour. It was then neutralized with 5N NaOH. The solution was clarified on a 5 µm membrane and purified on SEPHACRYL™ S400HR. Interesting fractions, corresponding to the "medium molecular size" (see Infection and Immunity, 70: 4433-4440 (2002)), were pooled and concentrated prior to de-N-acetylation treatment.

The solution was adjusted at 1M NaOH and left 24 hours at 37° C. After neutralization, the product was subjected to dialysis and concentration.

dPNAG Activation

S-GMBS (N-(γ-Maleimidobutyryloxy) sulfosuccinimide, Pierce) was added to dPNAG in 0.2M NaCl (ratio S-GMBS/PS (w/w):1/1) and incubated during 2 h at room temperature at pH 7.0 (pH regulation using 1M NaOH). Excess GMBS and by-products were removed by purification on TOYOPEARL® HW-40F using PBS, 10 mM EDTA, 50 mM NaCl pH 7.2 as elution buffer with a flow-rate fixed at 60 ml/h. The elution pool was selected in function of the optical density (UV=206 nm) and then concentrated on VIVASPIN® tubes 3,000 MWCO or AMICON™ Ultra 10,000 MWCO.

Coupling

GMBS-activated dPNAG and DTT reduced TT-SPDP were mixed and stirred at room temperature. According to the conditions used the reaction was quenched after 20-120 min by the addition of cysteine (4 mg/ml in Na phosphate buffer pH 8.0) for 30 minutes. The conjugate was clarified on 5 µm filter and injected on SEPHACRYL™ S300HR resin (XK16/100) for purification. Elution was realized in 200 mM NaCl with a flow-rate fixed at 30 ml/h. The elution fractions were analysed by hexosamine and by protein dosage. Interesting fractions were pooled and filtered on 0.22 µM STERIVEX™. The final conjugate was tested for polysaccharide (hexosamine dosage) and protein composition (Lowry dosage).

| Conjugate | N-acetylation level % | [dPNAG] mg/ml | [TT] mg/ml | PS scale (mg) | Coupl. time (min) |
|---|---|---|---|---|---|
| dPNAG-TT 010 | 10* | 15 | 15 | 30 | 120 |
| dPNAG-TT 011 | 10* | 12 | 24 | 20 | 120 |
| dPNAG-TT 012 | 10* | 17.5 | 35 | 22 | 80 |
| dPNAG-TT 019 | 34 | 5 | 10 | 10 | 20 |
| dPNAG-TT 020 | 34 | 2 | 2 | 10 | 20 |

*Not done on the lot used in the conjugation but estimated on a previous lot by NMR using the same de-N-acetylation method.

| Conjugate | In. TT/PS ratio (w/w) | F. TT/PS ratio (w/w) | Yield PS rec (%) | Filtration yield (%) |
|---|---|---|---|---|
| dPNAG-TT010 | 1/1 | 1.86/1 | 43 | 99 |
| dPNAG-TT011 | 2/1 | 2.86/1 | 56 | 99 |
| dPNAG-TT012 | 2/1 | 2.29/1 | 61 | 108 |
| dPNAG-TT019 | 2/1 | 1.45/1 | 81 | 97 |
| dPNAG-TT020 | 1/1 | 0.89/1 | 82 | 109 | dPNAG-SPDP:

A 5-fold molar excess of SPDP (N-Succinimidyl-3-(2-Pyridyldithio) Propionate, MW: 312.4, Pierce) dissolved in DMSO (dimethylsulfoxid, Merck) was added to 100 mg of dPNAG at 5 mg/ml in 100 mM Na phosphate, pH 7.2) and incubated 1 h at room temperature. Before purification on SEPHACRYL™ S100HR (XK16/40) the reaction mixture was concentrated to ±6 ml on AMICON™ Ultra 10,000 MWCO (centrifugation at 3000 rpm during 28 min). Elution was realized in phosphate buffer pH 7.4 with a flow-rate fixed at 60 ml/h. The interesting fractions (read at 206 nm) were pooled and concentrated to 1.1 ml on AMICON™ Ultra 10,000 MWCO (centrifugation at 3000 rpm during 30 min).

TT-SPDP:

A 15-fold molar excess of SPDP (Pierce) dissolved in DMSO (dimethylsulfoxid, Merck) was added to 1 g of TT (50 mg/ml) in 100 mM Na phosphate, pH 7.2 and incubated 80 min at room temperature. Then the product was injected on SEPHACRYL™ S100HR (XK16/40) and eluted in 100 mM Na acetate pH 5.6, 100 mM NaCl, 1 mM EDTA with a flow-rate fixed at 60 ml/h. The elution pool was selected in function of the optical density (UV=280 nm) and then concentrated to 19.6 ml on AMICON™ Ultra 10,000 MWCO (centrifugation at 3000 rpm during 75 min).

TT-LC-SPDP was produced as TT-SPDP but using LC-SPDP (Succinimidyl 6-[3-(2-pyridyldithio)-propionamido] hexanoate, Pierce) and an incubation time of 60 min.

TT-SH or TT-LC-SH

DTT was added to TT-SPDP or TT-LC-SPDP in a DTT/TT ratio (mg/mg) of 0.7/1. After 2 h at room temperature, the release of pyridine-2-thione was followed by its characteristic absorbance at 343 nm. The thiolated protein was purified from excess DTT by gel filtration (PD-10, Amersham). After concentration on AMICON™ Ultra 10,000 MWCO, protein content was estimated by Lowry dosage.

dPNAG-SPDP+TT-SH or TT-LC-SH (dPNAG-TT014 and 016)

Coupling was performed at room temperature under continuous stirring and with an initial TT/PS ratio (w/w) of 2/1.

dPNAG and TT-SH were mixed in order to obtain a final PS concentration of 20 mg/ml and a final protein concentration of 40 mg/ml. After 30 min, unreacted sulfhydryl groups were quenched by addition of 2-Iodoacetamide (Merck).

dPNAG and TT-LC-SH was mixed in order to obtain a final PS concentration of 10 mg/ml and a final protein concentration of 20 mg/ml. After 75 min, unreacted sulfhydryl groups were quenched by addition of 2-Iodoacetamide (Merck).

Then the conjugate is clarified using a 5 µm MINISART® filter and injected on SEPHACRYL™ S300HR (XK16/100). Elution was realized in 200 mM NaCl with a flow-rate fixed at 30 ml/h.

The elution fractions were analysed by hexosamine and by protein dosage. Interesting fractions were pooled and filtered on 0.22 µm STERIVEX™.

The resulting conjugates have a final TT/PS ratio (w/w) of 2.18 (TT-SH) and 2.24 (TT-LC-SH).

Thiolation of dPNAG 11.6 mg of DTT (1,4-Dithiothreitol, Boerhinger Mannheim, MW: 154.24) were added to 16.5 mg of dPNAG-SPDP. After 2 h at room temperature, the release of pyridine-2-thione was followed by its characteristic absorbance at 343 nm. The thiolated PS was purified from excess DTT by gel filtration (TOYOPEARL® HW40F) and then concentrated to 860 µl on AM ICON™ Ultra 10,000 MWCO.

dPNAG-SH+TT-SPDP (dPNAG-TT017)

Coupling was performed at room temperature under continuous stirring and with an initial TT/PS ratio (w/w) of 1.7/1.

dPNAG-SH and TT-SPDP were mixed in order to obtain a final PS concentration of 7.73 mg/ml and a final protein concentration of 13.3 mg/ml. After 90 min, unreacted sulfhydryl groups were quenched by addition of 2-Iodoacetamide (Merck).

Then the conjugate was clarified using a 5 µm MINISART® filter and injected on SEPHACRYL™ S300HR (XK16/100). Elution was realized in 200 mM NaCl with a flow-rate fixed at 30 ml/h.

The elution fractions are analysed by hexosamine and by protein dosage. Interesting fractions were pooled and filtered on 0.22 µm STERIVEX™.

The resulting conjugate has a final TT/PS ratio (w/w) of 2.74.

Example 3

Immunogenicity of S. aureus dPNAG-TT Conjugates

Groups of 30 mice were inoculated subcutaneously with S. aureus dPNAG-TT conjugates at a saccharide dose of 0.3 µg, either unadjuvanted or combined with a 3D-MPL adjuvant. The mice received three inoculations on days 0, 14 and 28. On day 41 serum was collected from the mice and each serum sample was tested by ELISA to assess the immune response against PNAG. Groups of 10 mice were used in the control groups and these were inoculated with saline.

Anti-PNAG ELISA:

Purified PNAG (2.5 µg/ml) mixed with methylated HSA (2.5 µg/ml) diluted in phosphate buffered saline (PBS) was coated on high binding microtitre plates (NUNC MAX-ISORP™) overnight at 4° C.

The plates were blocked with PBS-BSA 1%, 30 min at RT with agitation. The mice antisera were prediluted 1/100, then further twofold dilutions were made in microplates and incubated at 37° C. for 1 hour. After washing, bound murine antibody was detected using Jackson ImmunoLaboratories Inc. peroxidase-conjugated affiniPure Goat Anti-Mouse IgG (H+L) (ref: 115-035-003) diluted 1:5000 in PBS-BSA 02% TWEEN™ 0.05%. The detection antibodies were incubated for 30 min. at room temperature with agitation. The color was developed using 4 mg OPD (Sigma)+5 µl H2O2 per 10 ml pH 4.5 0.1M citrate buffer for 15 minutes in the dark at room temperature. The reaction was stopped with 50 µl HCl, and the optical density was read at 490 nm relative to 650 nm.

The results (shown in Table 1) were expressed in mid-point titers for the pooled sera. For individual sera analysis, a GMT was calculated on the mid-point titers of the 30 samples (10 for the controls).

TABLE 1

| Conjugate | Anti-PNAG midpoint titre Non-adsorbed | Anti-PNAG midpoint titre Adjuvant A |
|---|---|---|
| dPNAG-TT010 | 1371 | 28465 |
| dPNAG-TT011 | 1133 | 40899 |
| dPNAG-TT019 | 425 | 13429 |
| dPNAG-TT020 | 656 | 10080 |
| dPNAG-TT014 | 342 | 9806 |
| dPNAG-TT017 | 203 | 8094 |
| dPNAG-TT012 | 398 | 40509 |
| dPNAG-TT016 | 719 | 7937 |
| Control | 50 | 50 |

The invention claimed is:

1. A process of conjugating an isolated staphylococcal poly-N-acetylglucosamine (PNAG) which is less than 40% N-acetylated to a carrier protein comprising the steps of:
    a) activating the PNAG by adding a linker comprising a maleimide group to form an activated PNAG, wherein the weight/weight ratio of the PNAG to the linker comprising the maleimide group is 1:2-2:1;
    b) activating the carrier protein by adding a linker with a spacer length of 10-25 Angstroms, wherein the linker comprises a sulphydryl group, to form an activated carrier protein, wherein the weight/weight ratio of the carrier protein to the linker comprising the sulphydryl group is 15:1 to 5:1; and
    c) reacting the activated PNAG and the activated carrier protein to form a PNAG-carrier protein conjugate, wherein the weight/weight ratio of the activated PNAG to the activated carrier protein is 4:1-1:4.

2. The process of claim 1 wherein the linker comprising the maleimide group is attached to an amine group on the PNAG in step a).

3. The process of claim 1 wherein the linker comprising a maleimide group is selected from the group consisting of N-(β-Maleimidopropyloxy) succinimide ester (BMPS), N-[e-Maleimidocaproyloxy]succinimide ester (EMCS), N-[Gamma-Maleimidobutyryloxy]Succinimide (GMBS), m-Maleimidobenzoyl-N-hydroxysuccinimide ester) (MBS) Succinimidyl-4-(N-maleimidomethyl)cyclohexane-1-carboxylate (SMCC), long chain (LC)—SMCC (LC-SMCC), N-Succinimidyl 4-(4-maleimidophenyl)butyrate (SMPB), succinimidyl-6-(β-maleimidopropionamido) hexanoate (SMPH), Sulfo-EMCS, Sulfo-MBS, Sulfo-SMCC, Sulfo-GMBS and Sulfo-SMPB.

4. The process of claim 1 wherein the linker comprising the sulphydryl group is attached to an amine group on the carrier protein in step b).

5. The process of claim 1 wherein the linker comprising the sulphydryl group is selected from the group consisting of succinimidyl 6-(3-[2-pyridyldithio]-propionamido)hexanoate (LC-SPDP), succinimidyl 6-[α-methyl-α-(2-pyridyldithio)toluamido]hexanoate (LC-SMPT), Sulfo-LC-SMPT, and Sulfo-LC-SPDP.

6. The process of claim 1 wherein the carrier protein is selected from the group consisting of tetanus toxoid, diphtheria toxoid, diphtheria toxoid CRM197, Pseudomonas exoprotein A (rEPA), and Haemophilus influenzae protein D.

7. A process of making an immunogenic composition comprising carrying out the process of claim 1 and a further step of combining the PNAG-carrier protein conjugate with a pharmaceutically acceptable excipient.

8. The process of claim 7 comprising a further step of combining the PNAG-carrier protein conjugate with an additional antigen(s).

\* \* \* \* \*